United States Patent [19]
Jaworek et al.

[11] 4,038,140
[45] July 26, 1977

[54] PROCESS FOR BINDING BIOLOGICALLY ACTIVE PROTEINS

[75] Inventors: Dieter Jaworek, Weilheim; Joseph Maier, Pocking; Michael Nelböck-Hochstetter, Tutzing, all of Germany

[73] Assignee: Boehringer Mannheim G.m.b.H., Mannheim-Waldhof, Germany

[21] Appl. No.: 582,495

[22] Filed: May 30, 1975

[30] Foreign Application Priority Data

June 4, 1974 Germany .............................. 2426988

[51] Int. Cl.² .......................... C12K 1/00; C07G 7/02; C08L 5/00
[52] U.S. Cl. ......................................... 195/63; 195/68; 195/DIG. 11; 260/8; 260/17.4 GC
[58] Field of Search ........................... 260/8, 17.4 GC; 195/DIG. 11, 63, 68

[56] References Cited

U.S. PATENT DOCUMENTS

| | | | |
|---|---|---|---|
| 3,625,827 | 12/1971 | Wildi et al. .............................. | 195/68 |
| 3,764,477 | 10/1973 | Lehmann et al. ....................... | 195/68 |

OTHER PUBLICATIONS

Advances in Macromolecular Chemistry, vol. 2, pp. 1–87 (1970).

*Primary Examiner*—V. P. Hoke
*Attorney, Agent, or Firm*—Burgess, Dinklage & Sprung

[57] ABSTRACT

Biologically active proteins are bound onto an insoluble carrier by reacting such protein in an aqueous phase with a carrier comprising an activated polysaccharide having a hydrophilic graft co-polmyer grafted thereinto.

15 Claims, No Drawings

PROCESS FOR BINDING BIOLOGICALLY ACTIVE PROTEINS

The present invention relates to a process for binding biologically active proteins onto an insoluble carrier. More specifically, the invention provides a reaction in an aqueous phase of at least one such protein with an activated carrier material.

Biologically active proteins are promising substances for the discovery of new and improved biochemical processes. Thus, for example, enzymes belong to the most effective and specific catalysts which are able to catalyze a large number of commerically extremely interesting reactions. However, the use of biologically active proteins in technical processes is hindered by their high price and their low stability. Nevertheless, these disadvantages can, in principle, be partially or wholly overcome by binding the enzymes onto insoluble carriers. In particular, fixing to carriers makes it possible to reuse the enzymes repeatedly and, in many cases, makes it possible, for the first time, to use the active proteins technically. Furthermore, in many cases the stability of the active proteins can be increased by binding to carriers.

Known carrier materials which have proved to be very useful for immobilizing biologically active proteins are those based on polyacrylamide and polydextran. Because of their hydrophilic properties, the low exchange conditions between the carrier and the protein, as well as the possibility of influencing the pore diameter of the carrier by appropriate cross-linking, they fulfill many requirements which are demanded of protein carriers.

By variation of the matrix of such carriers, optimum properties can be achieved for special purposes. In many cases, this takes place by making use of copolymers based on acrylamide. Thus, a cross-linked polyacrylamide matrix is known which contains maleic acid or a derivative thereof as co-monomer. It can be readily cross-linked by cross-linking agents such as N,N'-methylene-bis-acrylamide, since such cross-linking agents readily co-polymerize with acrylamide and the dicarboxylic acid can easily be activated, via the cyclic anhydride derivative, simply by heating. In the case of such co-polymers, the influence of the groups which are still charged after covalent bonding of the active proteins is low so that the pH optima and the kinetic parameters of the enzymes also remain almost unchanged. Such carriers also have the advantage that the substrate and the reaction product, as well as the non-covalently bound biologically-active protein, are scarcely absorbed. However, a disadvantage of such carriers with an anhydride group for fixing the protein is that, with sensitive proteins consisting of sub-units, especially with many enzymes, in some cases satisfactory activity yields cannot be obtained, the specific activities (U/g.) are too low and the carrier-bound protein has an insufficient stability.

Another known method is the mechanical inclusion of proteins into cross-linked polyacrylamide. A disadvantage of this process is the slow bleeding of the protein from the gel matrix so that this process has not been widely used. The bleeding of proteins fixed by inclusion is dependent upon the cross-linking of the carrier, the pore structure, the mechanical loading and the ionic strength of the buffers used. However, an advantage of this process is that even sensitive enzymes consisting of sub-units, for example lactate dehydrogenase, catalase, hexokinase and glucose-6-phosphate dehydrogenase, can be bound with good activity yields. In the case of such an inclusion of a protein in a cross-linked polyacrylamide gel, the kinetic properties of the enzyme also remain substantially uninfluenced, at least with regard to low molecular weight substrates.

An improvement of the known methods of fixing biologically active proteins to carriers was achieved with the introduction of a two-stage process in which, in a first stage, the protein is reacted with a bridge building compound which contains at least one functional group capable of forming a bond with a carrier and at least one group which acylates or alkylates protein in aqueous solution, whereafter the product formed is either bound to an already pre-formed carrier or is fixed, as co-monomer, in a polymerization reaction with the formation of the actual carrier. In comparison with the mechanical inclusion of proteins into carriers, this process of protein co-polymerization has the advantage that, as a result of the covalent bond, bleeding is prevented, especially high activity and protein yields are achieved and covalent bonding takes place in statistical distribution not only of higher but also of smaller molecular weight materials.

The following Table I shows, using as an example the enzymes glucose oxidase (GOD) and D-hydroxynitrile lyase (D-Hy-Ly), how different carrier materials, which are all based on an acrylamide polymer, give quite different activity yields. In such case, the enzyme-carrier ratio was 0.033:1 g..

Table I

| carrier material | nature of the fixing | specific activity (U/g.) GOD | specific activity (U/g.) D-Hy-Ly |
|---|---|---|---|
| acrylamide-maleic acid copolymer | anhydride | 10 | 1.3 |
| polyacrylamide | mechanically included | 80 | 2.3 |
| polyacrylamide | protein co-polymer | 500 | 13 |

The polysaccharides represent a further large group of carriers for binding biologically-active proteins. Hitherto, they have essentially been used according to two methods:
1. fixing via activated polysaccharides, and
2. inclusion into cellulose derivatives, with simultaneous forming thereof (micro-encapsulation, wet spinning process).

In order to be able to produce a covalent bond, the polysaccharide has to be activated. For example, carboxymethyl cellulose azide was used, in which case the protein was bound, vis a peptide bond, with an activated carboxyl group. In the case of inclusion into cellulose derivatives, for example, cellulose triacetate, the proteins are present dissolved in vacuoles.

A disadvantage of the binding of active proteins onto activated polysaccharides, such as cellulose, cross-linked dextran, agarose and the like, is that, after completion of the protein binding, some of the groups are hydrolyzed and thus charged. Indeed, some of these carriers are so strongly charged that the greater part of the enzymes to be immobilized are absorptively held and the bound protein, depending upon the polyvalent character of the carrier, undergoes a shift of the pH optimum. A further disadvantage is the strong absorption of the substrate and the reaction product on such charged carriers.

This disadvantage can admittedly be overcome by inclusion fixing into regenerated cellulose derivatives but, because of the strong hindrance of diffusion, this process only permits the use of relatively small substrate molecules and the activity is quickly lost.

The present invention provides a process for binding biologically active products onto an insoluble carrier which does not suffer from the above-mentioned disadvantages and, in particular, also permits especially sensitive proteins consisting of sub-units to be fixed with high yields, provides a good stability of the bound proteins, is adaptable with regard to the mechanical properties and satisfies the requirements for technical use.

The present invention provides a process for binding biologically-active proteins onto an insoluble carrier comprising essentially, reacting at least one such protein in aqueous phase with an activated carrier based on a polysaccharide, wherein, the carrier is an activated polysaccharide graft-polymerized with a hydrophilic graft co-polymer.

Polysaccharide graft polymers are known. A comprehensive description of their properties and their chemistry is given in "Advances in Macromolecular Chemistry". Vol. 2, pub. Academic Press, London and New York 1970. Polysaccharide graft co-polymers prove to be especially suitable as carrier materials for the binding of biologically active proteins. They are preferably used as carriers in such a manner that the graft reaction takes place in the presence of the biologically active protein to be bound, whereby, depending upon the selected reaction conditions, not only a covalent bonding of the protein but also a simple inclusion thereof can take place. In other words, the graft co-polymerization of the hydrophilic monomers based on polysaccharide is carried out in the presence of the biologically active protein to be bound, with the simultaneous binding thereof.

According to an especially preferred embodiment of the process of the present invention, proteins, activated polysaccharide and hydrophilic monomer or monomers to be grafted on and possibly also cross-linking agents are brought together in aqueous phase, whereafter the graft co-polymerization is carried out. There are thus obtained inclusion-fixed biologically active proteins with, in comparison with previously known methods for inclusion fixing, improved activity yields, improved stability and improved accessibility for substrates.

According to another especially preferred embodiment of the process according to the present invention, the protein, together with a bridge-building compound which contains at least one co-polymerizable group and at least one group acylating or alkylating protein in aqueous solution, is reacted and the reaction product is brought together with the activated polysaccharide and the hydrophilic monomor or monomers to be grafted on and possible cross-linking agents in aqueous phase, whereafter the graft co-polymerization is carried out. This process variant gives co-valiently bound proteins with especially high activity yields.

Examples of biologically active proteins which can be used according to the process of the present invention include enzymes, enzyme associations, protein and peptide hormones, antigens, anti-bodies and the like.

Polysaccharides which can be used according to the present invention include, for example, starch, cellulose and cellulose derivatives, such as cellulose acetate, cellulose butyrate, allyl cellulose, carboxymethylcellulose, deoxythiocellulose methyl cellulose, hydroxyalkyl cellulose, regenerated cellulose, allyl starch, carboxymethyl starch, dialdehyde starch, the corresponding dextran derivatives, polyglucosides and the like. A summary of the polysaccharides which can be used for the graft polymerization and appropriate graft polymerization methods are also to be found in the above-mentioned literature reference from "Advances in Macromolecular Chemistry".

The activation of the polysaccharide necessary for the graft polymerization can take place by the introduction of a double bond, for example, by reaction with a bifunctional compound which contains a co-polymerizable olefinic double bond and a group which is reactive with hydroxyl groups, for example, an epoxide group, episulphide group, cycloimine group or lactam group, or by ionizing irradiation with the formation of long-life radicals or also by radical formation on the hydroxyl groups of the starch with a 1 electron acceptor, such as $Ce^{IV}$.

It is important that the activation permits a graft co-polymerization in aqueous phase with the hydrophilic monomer or monomer mixture to be grafted on. Activation thereby preferably takes place by reaction with a bifunctional compound in such a manner that the polysaccharide is made water-soluble. However, within the scope of the present invention, water-insoluble, activated polysaccharides can also be used for making carrier bound active proteins.

Expecially preferred difunctional compounds for the activation of the polysaccharide are activated allyl derivatives, such as allyl halides, for example allyl bromide, and activated acrylic or methacrylic acid derivatives, such as the acid chlorides, anhydrides, azides and the like, as well as activated dicarboxylic acid derivatives, such as chloromaleic acid. Other known alkylation and acylation monomers can also be used.

Examples of co-monomers which can be used for the grafting include acrylamide, acrylonitrile, vinyl acylates, such as vinyl acetate, propionate and phosphate, acrylates, methacrylates, allyl citrate, polyalkyleneglycol acrylates and methacrylates, N'-vinyl-lactams, such as N-vinyl-pyrrolidone, and N-substituted acrylamides and methacrylamides. The monomers preferably possess at least one carboxyl, aminocarbonyl, sulpho or sulphamoyl group, acrylamide being especially preferred.

The monomer to be grafted on can be a single hydrophilic co-polymerizable monomer or a mixture of several such monomers. Difunctional cross-linking agents can also be employed which must possess at least two olefinic double bonds capable of co-polymerization and which are preferably also hydrophilic. Examples of cross-linking agents include diacrylates, dimethacrylates, diacrylamides, such as N,N'-methylene-bis-acrylamide, the corresponding methacrylic compounds and the like.

As already mentioned, the process according to the present invention can be carried out in such a manner that first a graft co-polymer is prepared based on a polysaccharide and subsequently a biologically-active protein is fixed hereon. Thus, for example, for the grafting there can be used a mixture of acrylamide or methacrylamide and maleic acid or ethylene-maleic acid. By heating the graft polymer obtained, dicarboxylic acid anhydrides are formed which are then able to couple in aqueous solution with the biologically active protein. Such methods of fix are described, for example, in German Patent Specification No. 1,935,711.

In a further embodiment of the process according to the present invention, which is preferred, graft co-polymerization takes place in the presence of the protein to be bound. As already mentioned above, this can take place by covalent binding or by inclusion fix.

In the case of inclusion fix, with the mechanical binding of the protein, it is merely necessary to prepare a solution of the protein with the hydrophilic monomer and the activated polysaccharide and then to carry out the co-polymerization reaction, for example by the addition of conventional radical-forming initiators and accelerators. By the addition of cross-linking agents, the pore width of the product, which is in the form of a three-dimensional sieve, can be regulated as desired and adapted, for example, to the size of the protein to be fixed or to the size of its substrate or of its reaction product. Expecially preferred activated polysaccharides for this mode of use include the allyl ethers and the acrylic acid, methacrylic acid and maleic acid esters of starches and dextrans. However, other polysaccharides can also be employed in the same way, especially ionized polysaccharides.

According to a further preferred embodiment of the process according to the present invention, the graft co-polymerization does not take place in the presence of the unmodified biologically active protein, as in the case of the above-described embodiments, but in the presence of a protein reaction product with a bridge-building compound. Bridge-builders of this type, which are also called "coupling compounds", have at least one co-polymerizable olefinic double bond or another function capable of forming a covalent bond with the grafted on side chain in aqueous solution and a group which acylates or alkylates proteins in aqueous solution. Preferred acylating or alkylating groups according to the present invention include epoxy groups, ethylene-imine groups, halide groups activated by unsaturation, acid halide groups, amide groups, acid anhydride groups, aldehyde groups and oxazolone groups, as well as derivatives derived from carboxyl groups in which the OH group is replaced by one of the groups set out in pages 3 to 5 of published German Patent Specification No. 2,260,185.

Preferred coupling compounds include, for example, maleic anhydride and the homologues thereof in which the hydrogen atoms of the olefinic double bond are replaced by acyl groups containing up to 6 carbon atoms, allyl halides, especially allyl bromide and its homologues, acrylyl chloride and its homologues in which the hydrogen atoms are replaced by one or more lower alkyl radicals, the corresponding methacrylic acid compounds, maleic and fumaric acid chlorides and their homologues corresponding to the above definition, such as maleic anhydride and maleic acid azide, ethylene-imine compounds, such as 1-allyloxy-3-(aziridin)-propan-2-ol, epoxides, such as 2,3-epoxypropoxy acrylate and methacrylate, vinyl sulphonic acid chloride and the like.

The polysaccharide graft co-polymers to be employed according to the present invention can, for the enzyme fix, also be subsequently activated, for example, by means of cyanogen bromide. Also in the case of this embodiment of the process according to the present invention, in comparison with the previously known similar methods, substantially superior yields and activities are achieved. For example, in the case of binding the enzyme acylase onto a carrier based on a polydextran (Sephadex G-25) activated with cyanogen bromide, depending upon the particle size of the carrier and with a weight ratio of enzyme to carrier of 1:10, specific activities were achieved between 0.6 and 2,2 U/g. If, however, a starch allyl ether-acrylamide co-polymer was used which had been activated in the same way with cyanogen bromide, then the specific activity was 120 U/g.

Very superior properties are also achieved when an active protein is bound with a bridge-building co-polymer onto the graft polymer based on polysaccharide, in comparison with a binding method in which the procedure used is comparable but, instead of the polysaccharide component, another cross-linking agent is used for the polymerizate of the hydrophilic monomer in the carrier. Merely by this exchange of the cross-linking agent of the activated polysaccharide for a conventional difunctional cross-linking agent, there are obtained substantially increased activity yields and increased specific activities, as well as improved mechanical properties.

The following Table II shows, for three different exzymes as biologically-active proteins, the activity yields and specific activities obtained in the case of binding onto a carrier according to the invention and onto a carrier comparable therewith but cross-linked in another way according to the two-stage process, with the use of a bridge builder.

TABLE II

| enzyme | ratio of co-monomers in the carrier g./g. | ratio of polymer: enzyme [1] g./g. | ratio of enzyme: bridge builder [3] mg./μl. | activity yield % | specific activity U/g. |
|---|---|---|---|---|---|
| D-hydroxy-nitrile lyase from almond powder | acrylamide: starch allyl ether 1:0.33 | 1:0.23 | 1:0.05 | 20 | 41 |
| " | acrylamide: N,N'-bis [2] 1:0.057 | 1:0.25 | 1:0.05 | 10 | 27 |
| trypsin | acrylamide: starch allyl ether 1:0.2 | 1:0.125 | 1:0.25 | 33 | 30 |
| " | acrylamide: N,N'-bis [2] 1:0.1 | 1:0.16 |  | 14 | 12 |
| yeast hexokinase | acrylamide: starch allyl ether 1:2 | 75:1 | 1:1 | 7 | 125 |
| " | acrylamide: N,N'-bis [2] 1:0.2 | 75:1 | 1:1 | 2.5 | 46 |

[1] referred to the protein used for the immobilizing
[2] N,N'-bis = N,N'-methylene-bis-acrylamide
[3] acrylic acid chloride was used as bridge builder.

The improved mechanical properties are achieved by the process of the present invention are demonstrated, for example, by the higher flow-through rates when the carrier-bound active proteins are used in column reactors. In the following Table III, acylase bound, according to the process of the present invention, onto starch allyl ether/acrylamide co-polymer is compared with acylase bound in the same manner onto cross-linked polyacrylamide.

TABLE III

| carrier | specific activity U/g. | particle size mm. | gel bed diameter cm. | gel bed height cm. | flow-through rate [1] ml./min. |
|---|---|---|---|---|---|
| cross-linked polyacrylamide | 130 | 0.2–0.4 | 1 | 10 | 4 |
| starch allyl ether/acrylamide | 138 | 0.2–0.4 | 1 | 10 | 12 |

[1] 0.5M d,1-N-acetyl-alanine

In the process according to the present invention, by appropriate choice of the two components of the carrier, i.e., of the activated polysaccharide on the one hand, and of the graft co-monomer or of the graft co-monomer mixture, on the other hand, not only the binding behavior with regard to the active protein can be made to measure as desired but also the physical properties can be regulated in a similar manner. In general, the polysaccharide graft co-polymer used for the coupling should contain at least 20% by weight of grafted on hydrophilic comonomer units, in order to achieve a sufficiently stable carrier substance for normal handling. In certain special cases, however, it is also possible to use a proportion of polysaccharide of more than 80% in the graft co-polymer if especially easily deformable and soft products are desired. The graft co-polymer preferably contains 10 to 70% by weight of polysaccharide.

The following Examples illustrate the present invention and are not to be construed as limiting same.

EXAMPLE 1 — Preparation of the Activated Polysaccharide

Starch Allyl Ether

Starting materials:
40 g soluble starch
50 ml. acetone
150 ml. 5% aqueous sodium hydroxide solution
30 ml. allyl bromide Method:
The starch was slurried in 50 ml. acetone and added to the sodium hydroxide solution. The mixture was flushed with nitrogen and heated to 40° C. Then, within the course of 15 minutes, the allyl bromide was added dropwise, whereafter the reaction mixture was maintained at 55° C. until the reaction was neutral (50 minutes). In order to precipitate the allyl starch formed, the solution was cooled to 10° C. and mixed with 1 liter acetone. Water was removed from the viscous product so precipitated by intensively stirring it with 2 amounts of 250 ml. acetone, followed by drying. The yield of dry material was 42 g.

EXAMPLE 2

Starch Acrylic Ester

Starting materials:
10 g. Zulkowski starch 2N aqueous sodium hydroxide solution
4 ml. acrylyl chloride
5 ml. acetone Method:
Zulkowski starch was dissolved in 50 ml. water and the pH was adjusted to 9 with the sodium hydroxide solution. The solution was cooled to 4° C. and slowly mixed, within the course of 10 minutes, with a solution of the acrylyl chloride in 5 ml. acetone. The temperature and the pH were kept constant during the reaction. The starch acrylic ester formed was precipitated with acetone, washed and dried. The yield was 12 g.

Graft Co-polymerization and Simultaneous Protein Binding

EXAMPLE 3

Mechanical Inclusion

Starting materials:
3 g. acrylamide
2 g. starch allyl ether
600 mg. acylase, specific activity 20 U/mg.
2 ml. 5% ammonium peroxide disulfate (starter)
2 ml. 5% 3-dimethylaminopropionitrile Method:
The acrylamide, starch allyl ether and acylase were dissolved in 40 ml. phosphate buffer of pH 7.5. The solution was mixed with the starter and accelerator and flushed with nitrogen. After 5 minutes, gelling commenced. The gel was forced through a sieve of 0.4 mm. mesh size and eluted in a column with 5 liters 0.3M aqueous sodium chloride solution. The product had a specific activity of 26 U/g. The yield was 5 g.

EXAMPLE 4

Protein Co-polymerization (Co-valent Protein Binding with Bridge Builder

Starting materials:
6 g. acrylamide
2 g. starch allyl ether
1890 mg. D-hydroxynitrile lyase, specific activity 1 U/g.
0.1 ml. acrylyl chloride (bridge builder)
2 ml. 5% ammonium peroxydisulfate (starter)
2 ml. 5% 3-dimethylaminopropionitrile
50 ml phosphate buffer, pH 7.5; 0.2M Method:
The acrylamide and starch allyl ether were dissolved in 15 ml. phosphate buffer (Solution I). The hydroxynitrile lyase was dissolved in 35 ml. phosphate buffer, cooled to 4° C. and mixed with a similarly cooled solution of acrylyl chloride in 5 ml. diethyl ether. The mixture was intensively stirred for 30 minutes and subsequently added to Solution I. It was flushed with nitrogen until the greater part of the ether had been removed. The starter solutions were then added. After about 5 minutes, the reaction mixture begins to solidify. After the polymer has stood for at least 3 hours, it was forced through a sieve with a mesh size of 0.4 mm. and eluted in a column with 5 liters of 0.5M aqueous buffered sodium chloride solution. The yield was 8.4 g. The specific activity was 41 U/g. (lyophilisate) = about 345 U = 18% activity yield.

EXAMPLE 5. (comparison)

Protein Co-polymerization.

Starting materials:
7.5 g. acrylamide
0.4 g. N,N'-methylene-bis-acrylamide
1890 mg. hydroxynitrile lyase, specific activity 1 U/mg.
0.1 ml. acrylyl chloride
2 ml. 5% ammonium peroxydisulfate (starter)
2 ml. 5% 3-dimethylaminopropionitrile
45 ml. phosphate buffer, pH 7.5; 0.2M Method:

The acrylamide and N,N'methylene-bis-acrylamide were dissolved in 10 ml. phosphate buffer. The hydroxynitrile lyase was dissolved in 35 ml. phosphate buffer, cooled to 4° C. and mixed with a similarly cooled solution of the acrylyl chloride in 5 ml. ether. The mixture was intensively stirred and subsequently added to the first solution. The mixture was flushed with nitrogen until the greater part of the ether was removed. The starter solutions were then added. After about 5 minutes, the reaction mixture starts to solidify. After the polymer has stood for at least 3 hours, it was forced through a sieve with a mesh size of 0.4 mm. and eluted in a column with 5 liters of buffered 0.5M sodium chloride solution. The yield was 8.5 g. The specific activity is 27 U/g. (lyophilisate) = 230 U = 12% activity yield.

EXAMPLE 6

Protein Co-polymerization

Starting materials:
  8 g. acrylamide
  1.6 g. starch allyl ether
  1200 mg. trypsin (hog's pancreas)
  0.3 ml acrylyl chloride
  1.5 ml. 5% ammonium peroxydisulfate (starter)
  1.5 ml 5% 3-dimethylaminopropionitrile
  40 ml. phosphate buffer, pH 8.7; 0.4M Method:
The acrylamide and starch allyl ether were dissolved in 60 ml. water (Solution I). The trypsin is dissolved in the phosphate buffer, cooled to 4° C. and mixed with a similarly cooled solution of the acrylyl chloride in 40 ml. diethyl ether. The reaction mixture was intensively stirred for 30 minutes and subsequently added to Solution I. The mixture was flushed with nitrogen, whereby the greater part of the ether was removed. The starter solutions were then added. After about 15 minutes, the reaction mixture starts to solidify. After the polymer had stood for at least 3 hours, it was forced through a sieve with a mesh size of 0.4 mm. and eluted with 5 liters of buffered 0.5M sodium chloride solution. The yield was 8.2 g. The specific activity was 30 U/g. (lyophilisate) = 246 U = 41% yield.

EXAMPLE 7

Protein Co-polymerization

Starting materials:
  500 mg. trypsin, specific activity 0.5 U/g.
  3 g. acrylamide
  0.3 g. N,N'-methylene-bis-acrylamide
  0.1 ml. acrylyl chloride
  0.5 ml. 5% 3-dimethylaminopropionitrile
  0.5 ml. 5% ammonium peroxydisulfate (starter)

Method:
The trypsin was dissolved in 10 ml. 1M triethanolamine buffer (pH 8.5), cooled to 10° C. and flushed with nitrogen. While stirring, the acrylyl chloride, dissolved in 5 ml. diethyl ether, was added thereto and the reaction mixture further stirred for half an hour. Subsequently, the acrylamide and N,N'-methylene-bis-acrylamide, dissolved in 10 ml. water, as well as the starter accelerator were added to the reaction mixture. The solution solidifies to give a gel slurry which, after standing overnight, was forced through a metal sieve with a mesh size of 0.4 mm. The granulate was introduced into a column and eluted with 3 liters 0.2M phosphate buffer (pH 7.5) and subsequently lyophilized. The yield was 3 g. The specific activity was 12 U/g. The activity yield was 14%.

EXAMPLE 8

Protein Co-polymerization

Starting materials:
  2 g. starch allyl ether
  1 g. acrylamide
  40 mg. hexokinase
  10 mg. glucose
  0.04 ml acrylyl chloride
  0.5 ml. 5% 3-dimethylaminopropionitrile
  0.5 ml. ammonium peroxydisulfate Method:
As described in Example 4. The yield was 2.5 g. (lyophilizate). The specific activity was 80 U/g. The activity yield was 3.6%.

EXAMPLE 9

Protein Co-polymerization

Starting materials:
  3 g. acrylamide
  0.15 g. N,N'-methylene-bis-acrylamide
  40 mg. hexokinase, specific activity 140 U/g.
  10 mg. glucose
  0.04 ml acrylyl chloride
  0.5 ml. 5% 3-dimethylaminopropionitrile
  0.5 ml. 5% ammonium peroxydisulfate Method:
The hexokinase was centrifuged off, taken up with the glucose and 10 ml. 0.3M triethanolamine buffer (pH 8.0), cooled to 10° C. and flushed with nitrogen. The acrylyl chloride was dissolved in 5 ml. cold diethyl ether and slowly added dropwise thereto, while stirring. After an incubation period of about 30 minutes, the acrylamide and N,N'-methylene-bis-acrylamide, dissolved in 10 ml. 0.3M triethanolamine buffer (pH 8.0) was added thereto and the polymerization initiated by the addition of the catalysts. After completion of the polymerization overnight, the gel formed was forced through a metal sieve with a mesh size of 0.4 mm., transferred to a column and eluted with 0.2M phosphate buffer (pH 7.5) and subsequently lyophilized. The yield was 2.5 g. (lyophilizate). The specific activity was 45 U/g. The activity yield was 2%.

EXAMPLE 10

Protein Co-polymerization

Starting materials:
  600 mg. acylase I, hog's kidneys, specific activity 18 U/mg.
  3.5 g. acrylamide
  1.3 g. starch allyl ether
  44 ml TRIS buffer, pH 6.7, 0.3M
  0.02 g. cobalt chloride
  0.8 ml. allyloxy-(3-azididin-propan-2-ol)
  3.5 ml. 5% ammonium peroxydisulfate
  3.5 ml. 5% 3-dimethylaminopropionitrile Method:
The acrylamide, starch allyl ether and cobalt chloride were dissolved in 24 ml. TRIS buffer (Solution I). The acylase was dissolved in 20 ml. TRIS buffer and cooled to 4° C. The allyloxy-(3-aziridin-propan-2-01) was added thereto dropwise within the course of 10 minutes. After stirring for 30 minutes, Solution I was added to this solution. After the addition of the starter solution, the reaction mixture was flushed with nitrogen. The polymerization reaction commences after about 5 minutes. The gel obtained was, after standing for several hours, forced through a sieve with a mesh size of 0.4 mm. and then eluted in a column with 3 liters 0.3N aqueous sodium chloride solution (buffered to pH 7). The specific activity of the product is 138 U/g. and the particle size thereof was 0.2 - 0.4 mm.

It will be understood that the foregoing specification and examples are illustrative but not limitative of the present invention inasmuch as other embodiments within the spirit and scope of the invention will suggest themselves to those skilled in the art.

What is claimed is:

1. Process for binding a biologically active protein to an insoluble carrier which process comprises reacting at least one such protein in aqueous phase with a carrier comprising an activated polysaccharide with a hydrophilic graft co-polymer grafted thereinto, wherein said polysaccharide is activated by alkylation or acylation monomers, or by radical formation.

2. Process claimed in claim 1 wherein the graft co-polymerization of the hydrophilic monomer on the activated polysaccharide takes place in the presence of the protein upon simultaneous binding thereof to the carrier.

3. Process claimed in claim 2 wherein the protein, activated polysaccharide and hydrophilic graft co-monomer are contacted in aqueous phase.

4. Process claimed in claim 2 wherein the protein is first reacted with a linking compound containing a radical capable of acylating or alkylating protein in aqueous solution and a radical capable of copolymerization, and the resulting reaction product is contacted with said activated polysaccharide and graft co-monomer.

5. Process as claimed in claim 4 wherein a cross-linking agent is also added to the mixture of said reaction product, activated polysaccharide, and graft co-monomer.

6. Process as claimed in claim 1 wherein the hydrophilic graft co-monomer contains a minor portion of a monomer capable of direct bonding to a protein.

7. Process as claimed in claim 6 wherein the monomer capable of direct bonding to a protein is a dicarboxylic acid anhydride.

8. Process for binding a biologically active protein to an insoluble carrier which process comprises reacting at least one such protein in aqueous phase with a carrier comprising a polysaccharide with a hydrophilic graft co-polymer grafted thereinto, and subsequently activating said polysaccharide graft co-polymer by introducing a group capable of protein binding thereinto.

9. Process as claimed in claim 1 wherein said activated polysaccharide is selected from the group consisting of polysaccharide allyl ether, polysaccharide acrylic acid ester, polysaccharide methacrylic acid ester and polysaccharide maleic acid hemiester.

10. Process as claimed in claim 1 wherein the polysaccharide is selected from the group consisting of starch, cellulose derivatives, dextran derivatives and polyglucosides.

11. Process as claimed in claim 1 wherein the polysaccharide graft copolymer contains as the hydrophilic graft co-monomer a monomer consisting essentially of acrylamide.

12. Process as claimed in claim 1 wherein the biologically active protein is an enzyme.

13. Process as claimed in claim 1 wherein the biologically active protein is an enzyme association.

14. Process as claimed in claim 1 wherein the biologically active protein is a protein hormone, peptide hormone, antigen or anti-body.

15. Biologically active protein composition prepared by the process claimed in claim 1.

* * * * *